(12) United States Patent
Bierman (10) Patent No.: US 8,641,678 B2
(45) Date of Patent: *Feb. 4, 2014

(54) CATHETER SECUREMENT DEVICE

(75) Inventor: Steven F Bierman, Del Mar, CA (US)

(73) Assignee: Venetec International, Inc., Covington, GA (US)

( * ) Notice: Subject to any disclaimer, the term of this patent is extended or adjusted under 35 U.S.C. 154(b) by 289 days.

This patent is subject to a terminal disclaimer.

(21) Appl. No.: 13/094,723

(22) Filed: Apr. 26, 2011

(65) Prior Publication Data

US 2011/0202010 A1    Aug. 18, 2011

Related U.S. Application Data

(60) Continuation of application No. 12/648,149, filed on Dec. 28, 2009, now Pat. No. 7,935,084, which is a continuation of application No. 11/875,564, filed on Oct. 19, 2007, now Pat. No. 7,648,492, which is a division of application No. 10/677,757, filed on Oct. 1, 2003, now Pat. No. 7,354,421.

(60) Provisional application No. 60/415,728, filed on Oct. 1, 2002.

(51) Int. Cl.
*A61M 5/32* (2006.01)

(52) U.S. Cl.
USPC ............................. 604/174; 604/179; 604/180

(58) Field of Classification Search
USPC .............. 604/174–180; 128/DIG. 6, DIG. 26
See application file for complete search history.

(56) References Cited

U.S. PATENT DOCUMENTS

| 747,360 A | 12/1903 | Barry |
| 2,525,398 A | 10/1950 | Collins |
| 2,533,961 A | 12/1950 | Rouseau et al. |

(Continued)

FOREIGN PATENT DOCUMENTS

| CA | 995 995 | 8/1976 |
| CA | 2 281 457 | 2/2001 |

(Continued)

OTHER PUBLICATIONS

Multiple-Lumen Central Venous Catheterization Product With ARROW+gard™ Antiseptic Surface (Arrow International brochure) (Apr. 1994).

(Continued)

*Primary Examiner* — Bhisma Mehta
(74) *Attorney, Agent, or Firm* — Knobbe, Martens, Olson & Bear, LLP (57) ABSTRACT

A medical article securement device holds a medical article in position upon the body of a patient and can be used to inhibit lateral and longitudinal motion of the medical article. The securement device includes a retainer with a base and at least one post, and at least one cap. The cap is attached to the base of the retainer by a flexible connection, and can be placed into either a covered or uncovered configuration with respect to the post. The cap includes a recess which can receive a protrusion at the end of the post of the retainer. By placing the post through an appropriate opening in the medical article to be retained and then securing the medical article to the retainer by placing the cap into the covered position over the post, longitudinal and lateral motion of the medical article is inhibited.

18 Claims, 8 Drawing Sheets

(56) References Cited

U.S. PATENT DOCUMENTS

| | | |
|---|---|---|
| 2,707,953 A | 5/1955 | Ryan |
| 3,059,645 A | 10/1962 | Hasbrouck et al. |
| 3,064,648 A | 11/1962 | Bujan |
| 3,167,072 A | 1/1965 | Stone et al. |
| 3,394,954 A | 7/1968 | Sarns |
| 3,482,569 A | 12/1969 | Raffaelli |
| 3,529,597 A | 9/1970 | Fuzak |
| 3,602,227 A | 8/1971 | Andrew |
| 3,630,195 A | 12/1971 | Santomieri |
| 3,677,250 A | 7/1972 | Thomas |
| 3,686,896 A | 8/1972 | Rutter |
| 3,766,915 A | 10/1973 | Rychlik |
| 3,834,380 A | 9/1974 | Boyd |
| 3,847,370 A | 11/1974 | Engelsher |
| 3,856,020 A | 12/1974 | Kovac |
| 3,896,527 A | 7/1975 | Miller et al. |
| 3,900,026 A | 8/1975 | Wagner |
| 3,906,946 A | 9/1975 | Nordstrom |
| 3,920,001 A | 11/1975 | Edwards |
| 3,942,228 A | 3/1976 | Buckman et al. |
| 3,973,565 A | 8/1976 | Steer |
| 4,020,835 A | 5/1977 | Nordstrom et al. |
| 4,037,599 A | 7/1977 | Raulerson |
| 4,057,066 A | 11/1977 | Taylor |
| 4,059,105 A | 11/1977 | Cutruzzula et al. |
| 4,082,094 A | 4/1978 | Dailey |
| 4,084,911 A | 4/1978 | DeWitt |
| 4,099,744 A | 7/1978 | Kutnyak et al. |
| 4,114,618 A | 9/1978 | Vargas |
| 4,116,196 A | 9/1978 | Kaplan et al. |
| 4,123,091 A | 10/1978 | Cosentino et al. |
| 4,129,128 A | 12/1978 | McFarlane |
| 4,133,307 A | 1/1979 | Ness |
| 4,133,312 A | 1/1979 | Burd |
| 4,142,527 A | 3/1979 | Garcia |
| 4,161,177 A | 7/1979 | Fuchs |
| 4,170,995 A | 10/1979 | Levine et al. |
| 4,193,174 A | 3/1980 | Stephens |
| 4,224,937 A | 9/1980 | Gordon |
| 4,248,229 A | 2/1981 | Miller |
| 4,250,880 A | 2/1981 | Gordon |
| 4,316,461 A | 2/1982 | Marais et al. |
| 4,324,236 A | 4/1982 | Gordon et al. |
| 4,326,519 A | 4/1982 | D'Alo et al. |
| 4,362,156 A | 12/1982 | Feller, Jr. et al. |
| 4,392,853 A | 7/1983 | Muto |
| 4,397,647 A | 8/1983 | Gordon |
| 4,405,163 A | 9/1983 | Voges et al. |
| 4,449,975 A | 5/1984 | Perry |
| 4,453,933 A | 6/1984 | Speaker |
| 4,474,559 A | 10/1984 | Steiger |
| 4,480,639 A | 11/1984 | Peterson et al. |
| 4,516,968 A | 5/1985 | Marshall et al. |
| 4,517,971 A | 5/1985 | Sorbonne |
| 4,563,177 A | 1/1986 | Kamen |
| 4,585,435 A | 4/1986 | Vaillancourt |
| 4,633,863 A | 1/1987 | Filips et al. |
| 4,650,473 A | 3/1987 | Bartholomew et al. |
| 4,660,555 A | 4/1987 | Payton |
| 4,711,636 A | 12/1987 | Bierman |
| 4,742,824 A | 5/1988 | Payton et al. |
| 4,752,292 A | 6/1988 | Lopez et al. |
| 4,762,513 A | 8/1988 | Choy et al. |
| 4,792,163 A | 12/1988 | Kulle |
| 4,808,162 A | 2/1989 | Oliver |
| 4,823,789 A | 4/1989 | Beisang, III |
| 4,826,486 A | 5/1989 | Palsrok et al. |
| 4,838,858 A | 6/1989 | Wortham et al. |
| 4,852,844 A | 8/1989 | Villaveces |
| 4,857,058 A | 8/1989 | Payton |
| 4,863,432 A | 9/1989 | Kvalo |
| 4,869,465 A | 9/1989 | Yirmiyahu et al. |
| 4,880,412 A | 11/1989 | Weiss |
| 4,896,465 A | 1/1990 | Rhodes et al. |
| 4,897,082 A | 1/1990 | Erskine |
| 4,898,587 A | 2/1990 | Mera |
| 4,919,654 A | 4/1990 | Kalt |
| 4,932,943 A | 6/1990 | Nowak |
| 4,944,728 A | 7/1990 | Carrell et al. |
| 4,952,207 A | 8/1990 | Lemieux |
| 4,955,864 A | 9/1990 | Hajduch |
| 4,966,582 A | 10/1990 | Sit et al. |
| 4,976,700 A | 12/1990 | Tollini |
| 4,981,469 A | 1/1991 | Whitehouse et al. |
| 4,997,421 A | 3/1991 | Palsrok et al. |
| 5,000,741 A | 3/1991 | Kalt |
| 5,037,397 A | 8/1991 | Kalt et al. |
| 5,073,166 A | 12/1991 | Parks et al. |
| 5,073,170 A | 12/1991 | Schneider |
| 5,084,026 A | 1/1992 | Shapiro |
| 5,098,399 A | 3/1992 | Tollini |
| 5,112,313 A | 5/1992 | Sallee |
| 5,137,519 A | 8/1992 | Littrell et al. |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| 5,195,981 A | 3/1993 | Johnson |
| 5,226,892 A | 7/1993 | Boswell |
| 5,266,401 A | 11/1993 | Tollini |
| 5,267,967 A | 12/1993 | Schneider |
| 5,282,463 A | 2/1994 | Hammersley |
| 5,292,312 A | 3/1994 | Delk et al. |
| 5,304,146 A | 4/1994 | Johnson et al. |
| 5,306,243 A | 4/1994 | Bonaldo |
| 5,314,411 A | 5/1994 | Bierman |
| 5,322,514 A | 6/1994 | Steube et al. |
| 5,330,438 A | 7/1994 | Gollobin et al. |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,346,479 A | 9/1994 | Schneider |
| 5,352,211 A | 10/1994 | Merskelly |
| 5,354,282 A | 10/1994 | Bierman |
| 5,354,283 A | 10/1994 | Bark et al. |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,389,082 A | 2/1995 | Baugues et al. |
| 5,395,344 A | 3/1995 | Beisang, III et al. |
| 5,403,285 A | 4/1995 | Roberts |
| 5,413,562 A | 5/1995 | Swauger |
| 5,443,460 A | 8/1995 | Miklusek |
| 5,449,349 A | 9/1995 | Sallee et al. |
| 5,456,671 A | 10/1995 | Bierman |
| 5,468,228 A | 11/1995 | Gebert |
| 5,468,230 A | 11/1995 | Corn |
| 5,468,231 A | 11/1995 | Newman et al. |
| 5,470,321 A | 11/1995 | Forster et al. |
| D364,922 S | 12/1995 | Bierman |
| 5,484,420 A | 1/1996 | Russo |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,522,803 A | 6/1996 | Teissen-Simony |
| 5,527,293 A | 6/1996 | Zamierowski |
| 5,549,567 A | 8/1996 | Wolman |
| D375,355 S | 11/1996 | Bierman |
| 5,693,032 A | 12/1997 | Bierman |
| 5,697,907 A | 12/1997 | Gaba |
| 5,738,660 A | 4/1998 | Luther |
| 5,795,335 A | 8/1998 | Zinreich |
| 6,001,081 A | 12/1999 | Collen |
| 6,027,480 A | 2/2000 | Davis et al. |
| 6,213,979 B1 | 4/2001 | Bierman |
| 6,332,874 B1 | 12/2001 | Eliasen et al. |
| 6,491,664 B2 | 12/2002 | Bierman |
| 6,582,403 B1 | 6/2003 | Bierman et al. |
| 6,585,703 B1 | 7/2003 | Kassel et al. |
| 6,872,194 B2 | 3/2005 | Doyle et al. |

(56) References Cited

U.S. PATENT DOCUMENTS

| | | |
|---|---|---|
| 6,984,145 B1 | 1/2006 | Lim |
| 7,247,150 B2 | 7/2007 | Bierman |
| 7,354,421 B2 * | 4/2008 | Bierman .................. 604/174 |
| 7,648,492 B2 * | 1/2010 | Bierman .................. 604/513 |
| 7,935,084 B2 * | 5/2011 | Bierman .................. 604/174 |

FOREIGN PATENT DOCUMENTS

| | | |
|---|---|---|
| EP | 0247590 A2 | 12/1987 |
| EP | 356683 A | 7/1989 |
| GB | 2063679 | 6/1981 |
| GB | 2086466 A | 5/1982 |
| JP | S41-11535 | 5/1966 |
| JP | 1994-344852 | 12/1994 |
| JP | 1995-28563 | 5/1995 |
| WO | WO 80/01458 | 7/1980 |
| WO | WO 85/02774 | 7/1985 |
| WO | WO 91/16939 | 11/1991 |
| WO | WO 92/19309 | 11/1992 |
| WO | WO 96/10435 | 4/1996 |
| WO | WO 01/62328 | 8/2001 |

OTHER PUBLICATIONS

PCT International Search Report, Application No. PCT/US03/31251, Filing Date Oct. 1, 2003, mailing date Mar. 10, 2004.

* cited by examiner

CATHETER SECUREMENT DEVICE

RELATED APPLICATIONS

This application is a continuation of application Ser. No. 12/648,149, filed on Dec. 28, 2009, now issued as U.S. Pat. No. 7,935,084 on May 3, 2011, which is a continuation of application Ser. No. 11/875,564, filed on Oct. 19, 2007, now issued as U.S. Pat. No. 7,648,492 on Jan. 19, 2010, which is a divisional of application Ser. No. 10/677,757, filed Oct. 1, 2003, now issued as U.S. Pat. No. 7,354,421 on Apr. 8, 2008, which claims priority under 35 U.S.C. §119(e) to U.S. Provisional Patent Application Ser. No. 60/415,728, filed on Oct. 1, 2002, all of which are hereby expressly incorporated by reference in their entireties.

BACKGROUND OF THE INVENTION

1. Field of the Invention

This invention relates to a securement device for use with medical articles. More specifically, this invention relates to an anchoring system which releasably retains a catheter or other medical article in position upon a patient.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line may be secured to the patient in a variety of ways. One common way of securing a catheter is by taping the catheter or medical line to the patient.

Securing a catheter with tape upon the patient traditionally has certain drawbacks. The use of tape at the insertion site may retain dirt or other contaminant particles, potentially leading to infection of the patient. Additionally, removal of taped dressings may itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical line may additionally lead to the build up of adhesive residue on the outer surface of the catheter or medical line. This residue can result in contaminants adhering to the catheter itself, increasing the likelihood of infection of the insertion site. This residue may also make the catheter or medical line stickier and more difficult to handle for medical attendants.

An alternative to taped dressings is to provide a flexible clamp with winged extensions that are sutured to the patient's skin. In some applications, the winged extensions are integrally formed with catheter. In other applications, the flexible clamp is covered by a rigid fitting, which receives the catheter/clamp combination in a friction-fit manner. The rigid fitting and flexible clamp are formed with lateral, aligned holes, which allow the combination to be sutured to the patient's skin. Although suturing securely attaches the catheter to the patient, it is obviously painful and uncomfortable for the patient. These devices are also time consuming and inconvenient to secure, pose the risk of needle-stick to the healthcare worker, and risk suture-site infection to the patient.

For these reasons, a need exists for an improved way to secure catheters and medical lines to patients where the catheter may remain in place over an extended period of time and may be easily released from the securement device.

SUMMARY OF THE INVENTION

In accordance with one aspect of the systems and techniques described herein, a releasable medical line securement device is provided. The securement device includes a retainer having a base and an adhesive layer. The retainer also includes at least one post disposed upon the base of the retainer and extending away from a side of the base of the retainer opposite the side of the base of the retainer to which the adhesive layer is disposed. The post comprises a shaft and at least one protrusion disposed near the end of the shaft away from the base of the retainer.

In accordance with another aspect of the device, the retainer described above also includes at least one cap comprising a recess configured to receive the protrusion of the post. The cap is attached to the base of the retainer by a flexible connection such that the cap has at least two configurations including: a covered configuration in which the protrusion is disposed within the recess of the cap; and an uncovered configuration in which the protrusion is not disposed within the recess of the cap.

In accordance with a further aspect of the device, the retainer may comprise a second post and a second cap.

In accordance with another aspect of the device, the protrusion of the at least one post is held within the recess of the at least one cap in the covered configuration by a snap-fit arrangement between the protrusion and the cap.

In accordance with a different aspect of the systems and techniques discussed herein, a releasable medical article securement system is provided. The system comprises a medical article having an elongated body and at least one hole disposed to a lateral side of the elongated body, and a retainer. The retainer has a base and at least one post disposed upon the base of the retainer and extending away from the base. The post comprises a shaft and at a head disposed near the end of the shaft. The retainer also includes and at least one cap comprising a recess configured to receive the head of the at least one post. The cap is attached to the base of the retainer by a flexible connection, and has at least two configurations including a covered configuration in which the head of the post is disposed within the recess of the cap, and an uncovered configuration in which the head of the post is not disposed within the recess of the cap.

In accordance with one aspect of operation of the systems described herein, the at least one post of the retainer can be inserted through the hole of the medical article when the cap associated with the post is in the uncovered configuration, and the cap is placed into the covered configuration when the post is inserted through the hole of the medical article.

Another aspect of a technique in accordance with the disclosure of the medical devices described herein includes a technique for releasably securing a medical article to a patient. The method includes providing a medical article having an elongated body and at least one hole disposed to a lateral side of the elongated body, and providing an appropriate retainer. The cap of the retainer may then be placed in the uncovered configuration. The medical article can then be placed onto the retainer such that the post of the retainer is inserted through the hole of the medical article, and the cap of the retainer placed into the covered configuration.

For purposes of summarizing, certain aspects, advantages and novel features have been described herein. It is to be understood that not necessarily all such advantages may be achieved in accordance with any particular embodiment.

Thus, the systems described may be embodied or carried out in a manner that achieves or optimizes one advantage or group of advantages as taught herein without necessarily achieving other advantages as may be taught or suggested herein.

BRIEF DESCRIPTION OF THE DRAWINGS

The above mentioned and other features will now be described with reference to the drawings of the present securement system. The shown embodiments are intended to illustrate, but not to limit the invention. The drawings contain the following figures.

DETAILED DESCRIPTION

Described herein are the embodiments of an improved device for releasably securing medical articles such as catheters to a patient. The device includes an anchor pad for attaching the device to the skin of a patient. The device also includes a base disposed upon the anchor pad which includes retaining elements that operate to attach the device to a medical article, or a fitting of a medical article. Note that in some applications a fitting is itself releasably attached to a medical article and in other applications the fitting is integrally foiined with the medical article. The retaining elements generally inhibit relative movement between the medical article and the securement device in at least one degree of freedom. The securement device also includes caps attached to the base by flexible couplings such as leashes.

The following description and Figures describing various preferred embodiments are made to demonstrate various configurations of possible systems in accordance with the current invention. The embodiments illustrated can be used with a variety of medical devices, including various catheters that include wings with suture holes. One particular such catheter is the Arrow MAC™ catheter 500 (See FIG. 7) from Arrow International of Reading, Pa. This catheter 500 includes a catheter body 510 which provides a pair of lateral wings 520, 530, each of which includes a suture hole 540, 550 disposed to a lateral side of the elongated catheter lumens.

The applicability of the securement device described herein with any particular catheter, or the use of such a catheter in the description is not intended to limit the disclosed concepts to the specified embodiments or to usage with only those medical articles. In addition, various systems will be described in the context of an exemplary securement device incorporating the described systems and techniques. Those of skill in the art will recognize that the techniques described are neither limited to any particular type of securement device, nor to the securement of any particular type of medical article for every described aspect herein.

Figure 1:
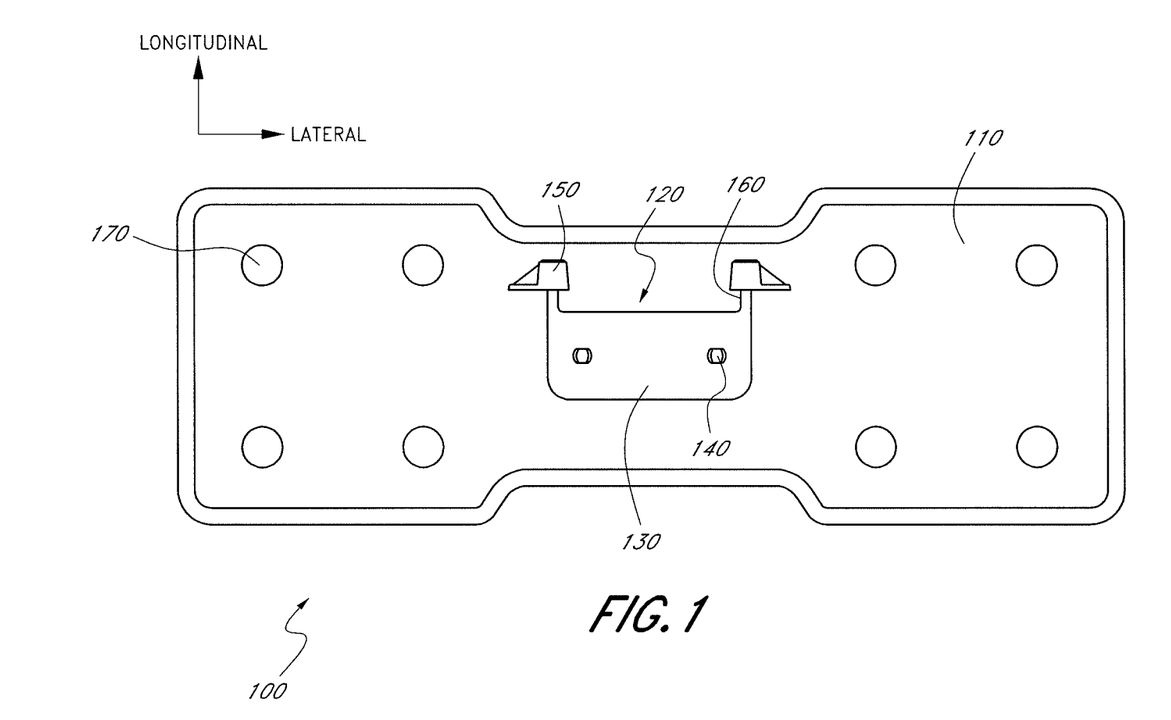
FIG. 1 is a top view of one embodiment of a securement device in accordance with this disclosure.
Figure 1A:
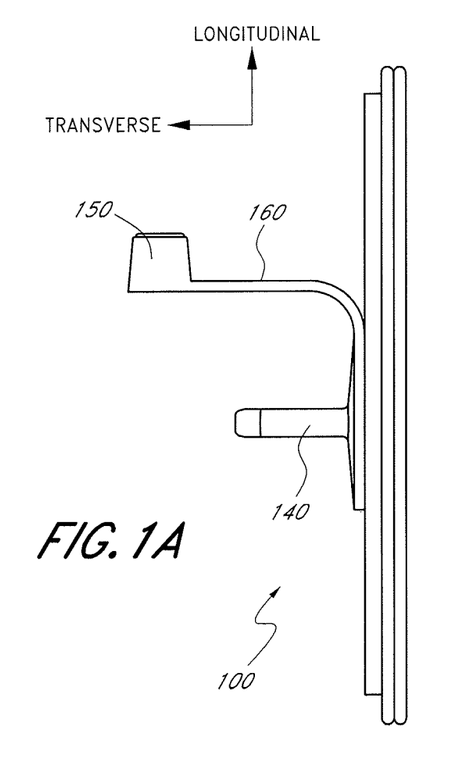
FIG. 1A is a side view of the device of FIG. 1.

To assist in the description of these components of the anchoring system (see FIG. 1), the following coordinate terms are used. A "longitudinal axis" is generally parallel to the portion of the connector fitting or other medical article retained by the securement system, as well as parallel to the axis of a retained medical line. A "lateral axis" is normal to the longitudinal axis and is generally parallel to the plane of an anchor pad, as seen in FIG. 1. A "transverse axis" extends normal to both the longitudinal and lateral axes (see FIG. 1A). In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of a catheter or the elongated portion of another retained medical article, and therefore is substantially synonymous with the term "longitudinal" as used herein. Also, the terms "proximal" and "distal", which are used to describe the present anchoring system, are used consistently with the description of the exemplary applications. Thus, proximal and distal are used in reference to the center of the patient's body. The terms "upper," "lower," "top," "bottom," and the like, which also are used to describe the present anchoring system, are used in reference to the illustrated orientation of the embodiment, and are illustrated on the enclosed FIGURES.

To facilitate a complete understanding of the invention, the remainder of the detailed description describes the invention with reference to the Figures, wherein like elements are referenced with like numerals throughout.

Overview

Prior to describing particular embodiments of the illustrated medical line securement systems, a brief overview explaining the major components of the system and its use will be presented. As shown by the exemplary medical line securement system of FIG. 1, the system can comprise a securement device 100 in two main components: an anchor pad 110 and a retainer 120. As noted above and discussed in greater detail below, the securement device 100 can form a component of a catheterization system that also includes one or more medical articles, such as connector fittings, catheter adaptors, fluid supply lines, or other articles suitable for securement via the anchor pad 110 and retainer 120.

Figure 4:
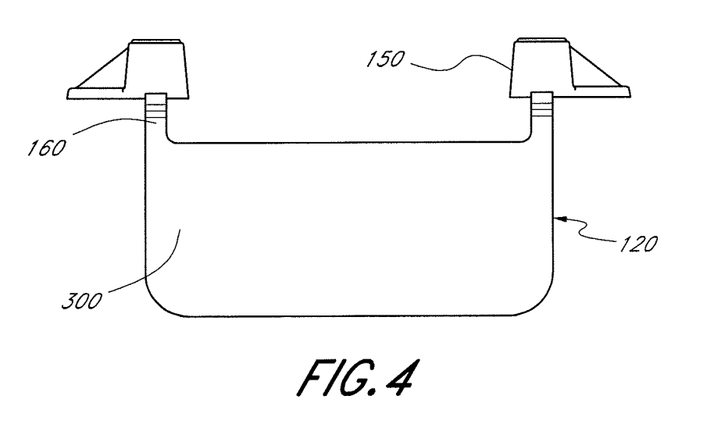
FIG. 4 is a bottom view of the base of the securement device of FIG. 1.
Figures 5, 6A:
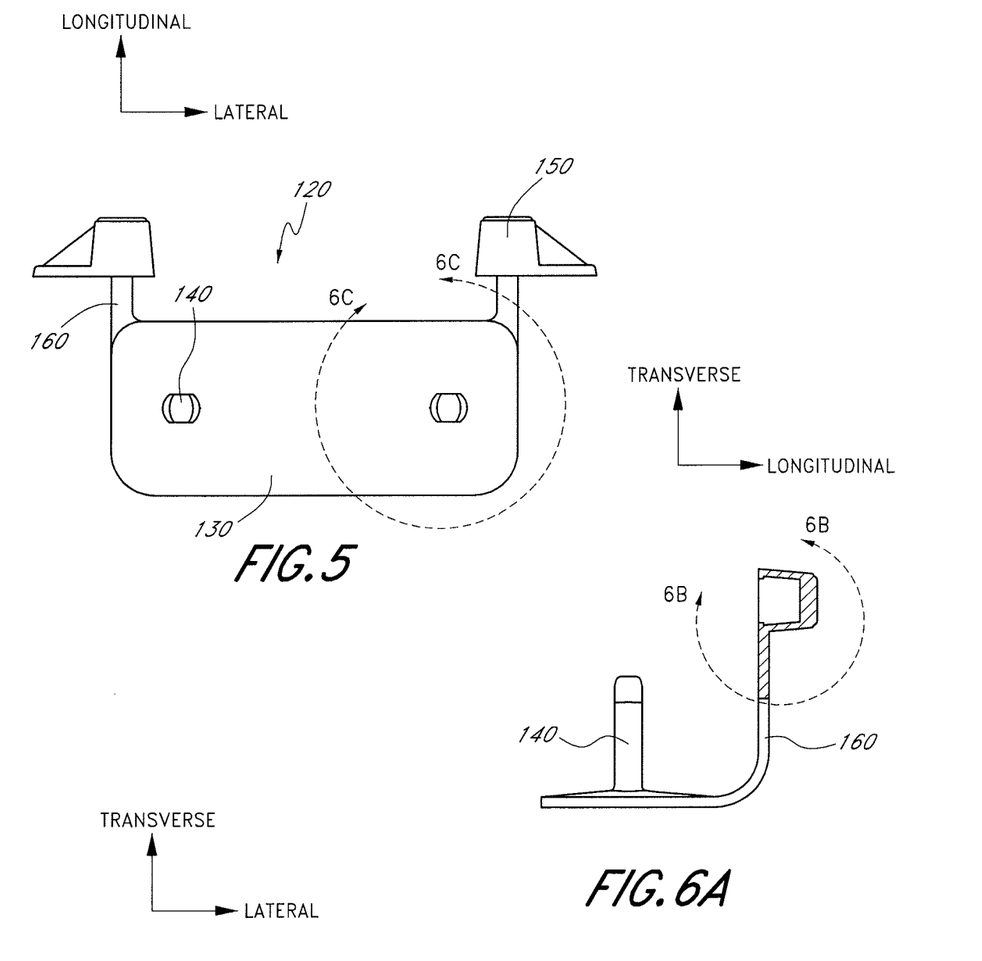
FIG. 5 is a top view of the base of the securement device of FIG. 1.
FIG. 6A is a detail section view of FIG. 6.
Figure 6:
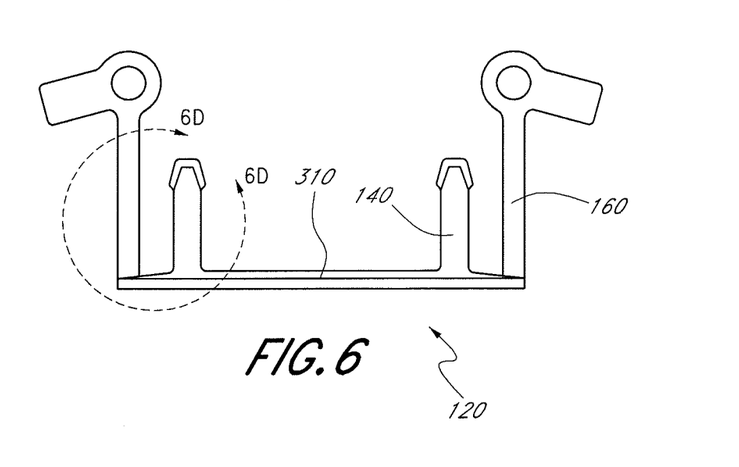
FIG. 6 is a front view of the base of FIG. 5.
Figure 6B:
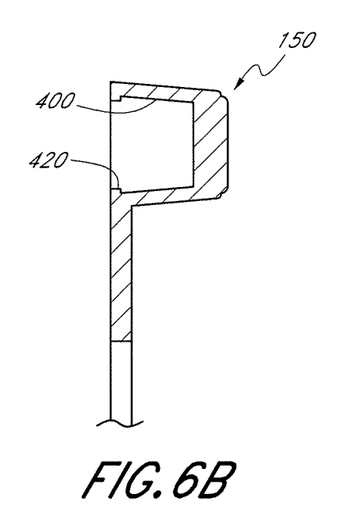
FIG. 6B is a detail view of region B of FIG. 6A.

The retainer 120 is mounted upon the anchor pad 110 and the anchor pad is secured to the skin of a patient, generally by an adhesive disposed upon the bottom surface of the pad. The retainer is configured to receive a medical article and secure it in position. An exemplary retainer 120, as shown in FIGS. 4-6, can comprise several sub-components, including a base 130, one or more posts 140, and one or more caps 150 corresponding to the posts 140. The caps are connected to the base 130 of the retainer by a leash 160 or other connection. The releasable engagement of a medical article is achieved, at least in part, by cooperation between the posts 140 and the caps 150. Because the caps 150 may be released from the posts 140 after the medical article is secured, it is possible for the medical article to be removed from the securement device 100 for any necessary purpose. This can include purposes such as replacing the securement device, replacing the medical line, or moving the patient. This removal of the medical article from the securement device can be accomplished without removing the device from the patient if desired.

Figure 7:
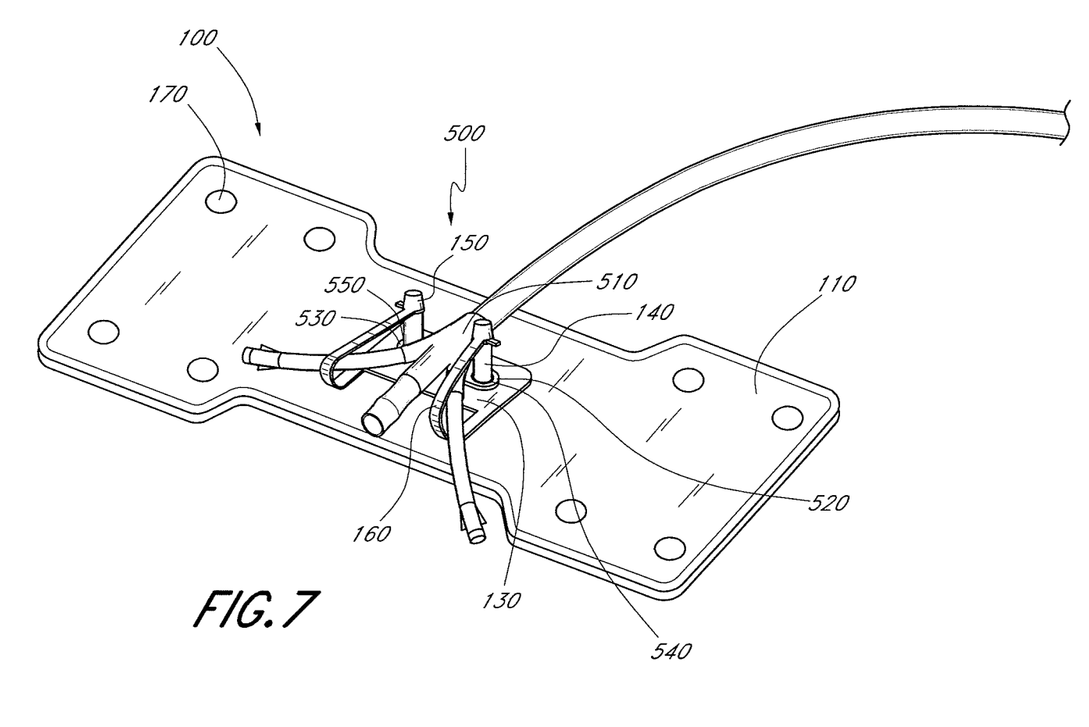
FIG. 7 is a perspective view of the securement device of FIG. 1 shown with the caps in the closed position and the exemplary catheter positioned in and retained by the retainer.

As is illustrated in FIG. 7, the retainer 120 can be used to hold a medical article 500 by placing the medical article 500 onto the base 130 of the retainer 120 in such a way that the posts 140 extend through one or more holes 540, 550 of the medical article. The caps 150 may then be secured in a covered position over the top of the posts 140 in order to prevent inadvertent disengagement between the medical article 500 and the retainer 120. Further examples will be provided in the description which follows.

When the caps 150 are placed in position over the posts 140 into the covered configuration, a medical article is inhibited from moving substantially in either the lateral or longitudinal directions by the interaction between the posts and the holes of the medical article.

The securement device 100 also desirably releasably engages the medical article. This allows the securement device to be disengaged from the medical article without removing the medical article from the patient for any of a variety of known purposes. For instance, the healthcare provider may wish to remove the securement device in order to change the anchor pad 110 or to clean the insertion site without removing the catheter and its associated fitting from the patient. In situations where a catheter is in position in the patient for an extended period of time, it is advantageous to periodically change the securement device in order to maintain the best positional securement of the catheter. For these purposes, it is desirable that the disengagement of the medical article from the securement device can be accomplished without removing the medical article from the patient.

Anchor Pad

Figure 2:
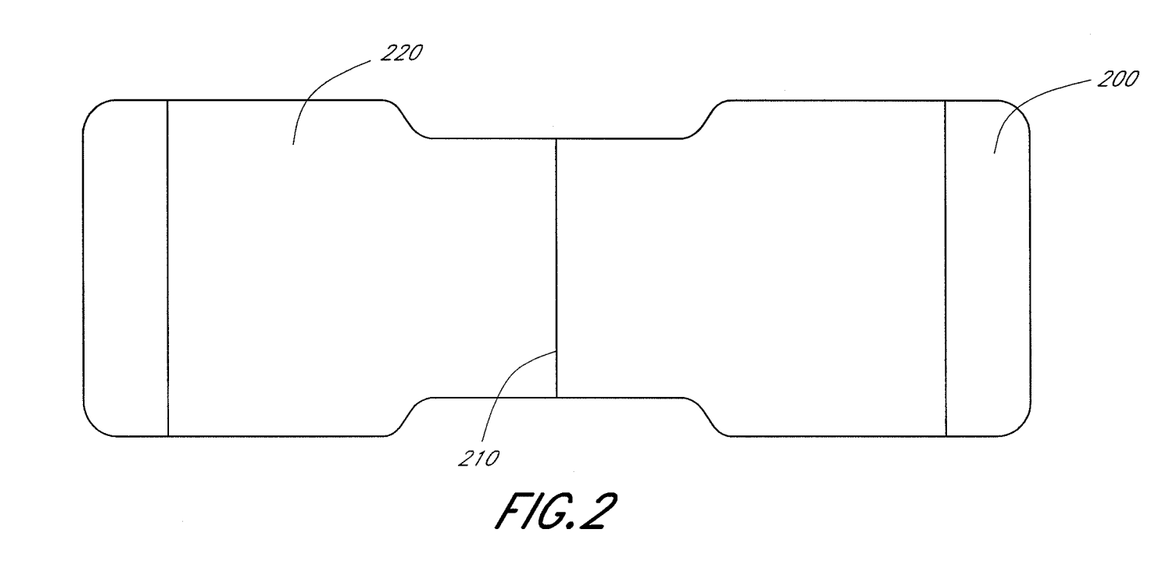
FIG. 2 is a top view of the anchor pad of the securement device of FIG. 1.
Figure 3:
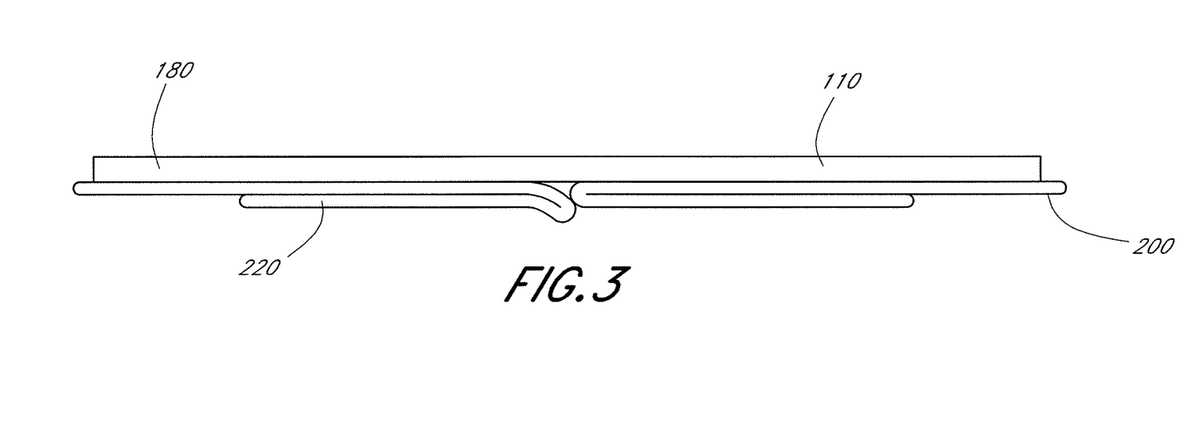
FIG. 3 is a front view of the anchor pad of FIG. 2.

As shown in FIGS. 1 to 3, an anchor pad 110 preferably comprises a laminate structure with an upper foam layer (e.g., closed-cell polyethylene foam), and a lower adhesive layer. The lower adhesive layer constitutes the lower surface of the anchor pad 110. The lower surface preferably is a medical-grade adhesive and can be either diaphoretic or nondiaphoretic, depending upon the particular application. Such foam with an adhesive layer is available commercially from Avery Dennison of Painsville, Ohio. The anchor pad can include holes 170 as illustrated (see FIG. 1), or can be formed without such holes. These holes can be used to suture the pad 110 to the skin of the patient in addition to, or as an alternative to, using the adhesive to attach the pad to the skin of a patient.

As a further alternative, a hydrocolloid adhesive can advantageously be used upon the anchor pad for attaching the anchor pad to the skin of the patient. The hydrocolloid adhesive has less of a tendency to excoriate the skin of a patient when removed. This can be particularly important for patients whose skin is more sensitive or fragile, such as those with a collagen deficiency. Other alternative devices may include the use of more than one type of adhesive on different portions of the lower surface of the anchor pad. This may be of particular use when the area of the anchor pad below the base 130 of the retainer 120 requires greater securement to the patient's skin.

As shown in FIG. 3, a surface of the upper foam layer constitutes an upper surface 180 of the anchor pad 110. The upper surface can be roughened by corona-treating the foam with a low electric charge. The roughened or porous upper surface can improve the quality of the adhesive attachment between the base 130 and the anchor pad 110. In the alternative, the flexible anchor pad can comprise a medical-grade adhesive lower layer, an inner foam layer and an upper paper or other woven or nonwoven cloth layer.

A removable paper or plastic release liner 200 preferably covers the adhesive lower surface before use. This is shown most clearly in FIG. 3. The liner 200 preferably resists tearing and preferably is divided into a plurality of pieces to ease attachment of the pad to a patient's skin. In the illustrated embodiment, the liner 200 is split along a center line 210 of the flexible anchor pad 110 in order to expose only half of the adhesive lower surface at one time.

The liner length, as measured in the lateral direction, extends beyond the center line of the anchor pad and is folded over, or back onto the liner itself. This folded over portion defines a pull tab 220 to facilitate removal of the liner 200 from the adhesive lower surface of the pad 110. A medical attendant uses the pull tab 220 by grasping and pulling on it so that the liner 200 is separated from the lower surface. The pull tab 220 overcomes any requirement that the medical attendant pick at a corner, edge or other segment of the liner 200 in order to separate the liner from the adhesive layer. The pull tab of course can be designed in a variety of configurations. For example, the pull tab need not be located along a center line of the anchor pad; rather, the pull tab can be located along any line of the anchor pad in order to ease the application of the anchor pad onto the patient's skin at a specific site. For example, an area of a patient's skin with an abrupt bend, such as at a joint, can require that the pull tab be aligned toward one of the lateral ends of the anchor pad rather than along the center line.

As seen most clearly in FIG. 2, the anchor pad 110 is generally configured so as to provide for a longitudinally narrower region near the lateral center of the pad, and regions of greater longitudinal size to each lateral side. This results in the center of the anchor pad 110 near the base 130 being more narrow, and the lateral sides of the anchor pad having more contact area. This can provide greater stability and adhesion to a patient's skin.

Base

The retainer 120 of the securement device 100 also includes a base 130. The base 130 is disposed upon the upper surface 180 of the anchor pad 110. The base 130 can comprise a substantially rigid member which is attached to the upper surface 180 of the anchor pad 110 by any of a variety of techniques. These can include the use of adhesives, ultrasonic welding, or any other technique known in the art. The base 130 preferably has sufficient lateral extent to provide a stable surface for attachment to the anchor pad, and also to provide a receiving area of sufficient space for a catheter or other medical article to rest upon the base when secured. It may be advantageous for this receiving area to provide a surface large enough to support the medical article in such a way that the retainer 120 cannot act as a fulcrum about which the medical article can bend or crimp.

As shown most clearly in FIGS. 4 and 5, the base 130 preferably takes the form of a flat plate or platform with a lower surface 300 that is bonded to the upper surface 180 of the adhesive pad 110. The base 130 can also include an upper surface 310, upon which retaining elements for interacting with some feature of the medical article to be retained can be disposed. This upper surface 310 in some applications can be flat, as shown in the figures. In other applications, the upper surface of the base can have a shape which is configured to cooperate with the shape of the retained medical article. For instance, if the medical article to be retained has a rounded shape, the upper surface of the base can have a corresponding rounded shape in order to more completely support the retained medical article.

In additional embodiments of the securement device (not illustrated), the base of the retainer can include a channel or other retaining structure in addition to that described above. Such retaining structure can be used to assist in properly positioning the medical article as it is held upon the retainer 120.

As shown in FIG. 6, these retaining elements can comprise a pair of posts 140 in the illustrated securement device 100. These posts extend upwardly, away from the upper surface 310 of the base 130. These retaining elements can be used to secure the medical article to the base 130 either directly or by way of a fitting (e.g., a box clamp or soft wing clamp). The posts can be inserted through appropriate openings (e.g., a hole or recess) in the fitting or in the medical article in order to secure the medical article upon the base. These openings can include suture holes or recesses in a fitting to which the medical article is attached. By placing the posts 140 through an opening (e.g., a hole) on the medical article, the securement device 100 inhibits movement of a catheter or other medical article at least in the longitudinal and lateral directions.

Figure 6C:
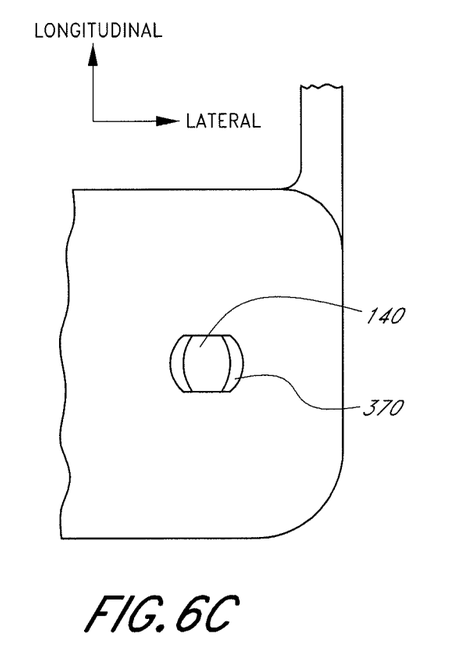
FIG. 6C is a detail top view of the base of FIG. 5.
Figure 6D:
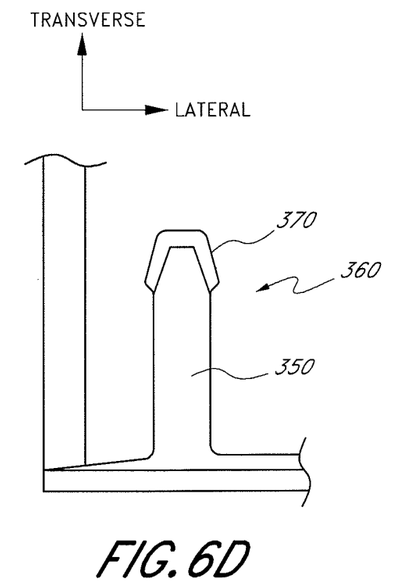
FIG. 6D is a detail front view of the post of the base of FIG. 6.

Note that for securement of catheters or medical articles of certain designs, it can be preferable to dispose more than two posts upon the base 130 of the device 100. For example, if a fitting with four openings were to be secured, it might be advantageous to present four posts extending from the base 130 at positions corresponding to each of the openings of the medical article fitting as is illustrated in FIG. 6F. In addition, the base 130 can be configured with fewer posts than the number of openings, as long as one or more posts are configured to interact with one or more of the available openings of the medical article or fitting.

As shown in FIG. 6, each post 140 can extend upwardly away from the base 130 of the retainer 120 and the body of the patient. Each post 140 includes a shank or shaft 350, attached to and extending upwardly from the upper surface 310 of the base 130 (see FIG. 6D). The posts 140 can have a variety of lengths and a variety of distances between them, depending upon the particular application and the particular fitting or medical article which they are to secure. The posts 140 are laterally spaced at least wide enough to accommodate the medical line or fitting to be secured. Preferably, the posts are spaced apart by a distance between 5 mm and 40 mm, and more particularly by a distance equal to about 21 mm. The shaft 350 of each post 140 has a diameter sufficient to perform its structural function, as described in more detail below, which will depend upon the material chosen for the base 130 and shafts 350. The illustrated posts comprise a polymer plastic material, with a diameter between 0.5 mm and 3 mm and particularly about 2 mm. All dimensions included herein are for illustration purposes only and are not intended to limit the disclosure to the particular dimensions recited.

At least one protrusion 360 extends radially away from the center of the shaft 350. In the illustrated device, the protrusion comprises an enlarged tip or head 370 at the transversely distal end of the shaft 350. As best seen in FIG. 6D, at least a portion of the head 370 of each post 140 is larger than the diameter of the shaft 350, preferably having a maximum diameter of 1.1 to 1.5 times the diameter of the shaft. In the illustrated device, the head 370 has a generally blunt truncated conical shape with a smooth surface and a maximum diameter at an overhanging lower surface or underside. It will be understood, however, that the head can take a variety of other shapes, such as for example, a hemisphere, a cone, an arrowhead, a barbed shape, a "mushroom" head, and such other types of radially projecting structures. A relatively blunt end of the head 370 is preferred to avoid snagging on materials such as a health care provider's latex gloves or sheets on the patient's bed. A slot (not shown in the illustrated device) can also be formed in the head of the post 140 in order to allow a space for the sides of the head 370 of the post to flex inwardly when subject to compression and improve the flexibility of the head 370 of the post 140.

Those of skill in the art will recognize that in some applications the posts 140 can differ from each another in size, shape and configuration. For example, the posts 140 could be constructed to have different heights from one another, or to have different diameters. In addition, the posts 140 could each have different shaped or sized heads 370, as discussed above. Furthermore, if more than two posts are used, a similar size or shape might be shared between two posts, but not by the remaining posts. For instance, a securement device in accordance with the current invention might have one short, thin post with a mushroom head, one tall, thin post with an arrow-shaped head, and one tall, thick post with a conical head having a slot.

Figure 8:
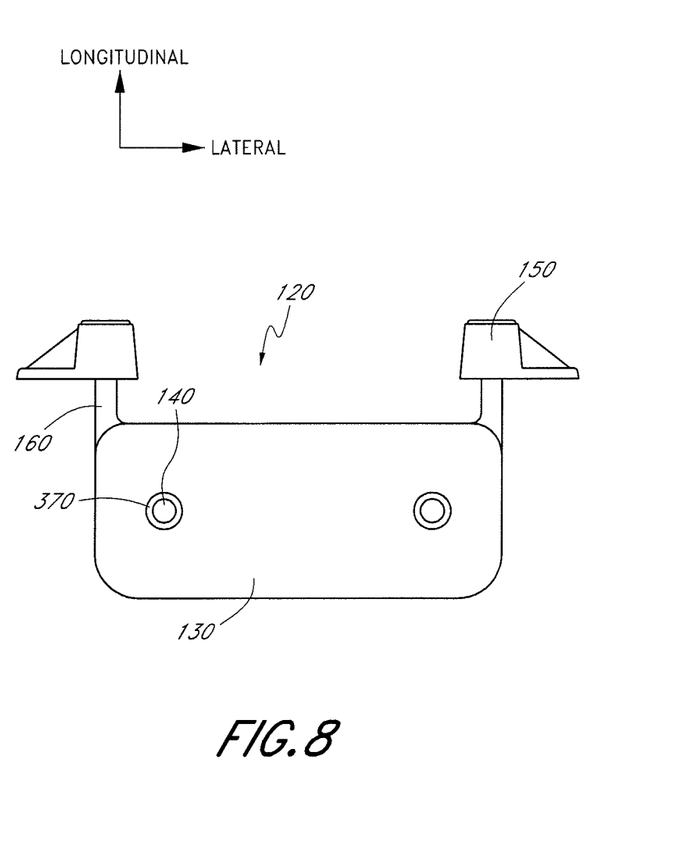
FIG. 8 is a top view of the base of the securement device of FIG. 1 and shows the protrusion extending to the same extent around the circumference of each post.

FIG. 8 is a top view of the base 130 of the securement device of FIG. 1 and shows the protrusion of the head 370 extends to the same extent around the circumference of each post 140. It should be noted that the protrusion need not extend in the same manner, or to the same extent, around the entire circumference of the post. For instance, in the illustrated securement device (shown most clearly in FIG. 6C), the protrusion extends in the lateral directions from each post 140, but not significantly in the longitudinal directions. As can be seen in the FIGURE, the protrusions of the head 370 are seen to not extend from the post in the longitudinal directions.

It should also be noted that the size of the protrusions of the posts 140 need not be larger than the size of the openings in the retained medical article or fitting. The medical article need not be snug against the post 140 or protrusion when the posts are inserted through the openings of the medical article or fitting. In many applications, it will be preferable for the medical article to not have any contact or interference with the post 140; the medical article is simply slipped over the posts. However, if there is contact or interference between the post 140 or protrusion and the medical article, the securement device can still operate in substantially the same manner. It may, however, be necessary for greater care to be taken when pressing the medical article over the posts of the device.

Cap

A cover or cap 150 for each post 140 is constructed as shown in FIGS. 5, 6, 6B and 6E. Each cap 150 is designed to be capable of being placed over the protrusion on the head 370 of one of the posts 140, and then snapped into position on top of the post 140. As shown most clearly in FIG. 6B, the cap in the illustrated embodiment has a generally hollow cylindrical shape, with an inner recess 400 that has an opening at the base of the cap 150 which exposes the recess 400. The opening is narrower than the recess 400 inside the cap, creating a collar 420 at the opening. In this way, when a cap 150 is pressed down over one of the posts 140, the head 370 of the post will tend to expand the opening of the cap 150 as it moves past the collar 420. Alternatively depending on the relative stiffness of the materials out of which the post 140 and cap 150 are constructed, the head 370 of the post 140 may flex inwardly or deform in order to fit through the collar 420 of the cap 150. This can be facilitated by using a post design that includes a slot, as described above, to allow more flexibility in the head 370 of the post 140.

Once the head 370 is received within the recess 400 inside the cap 150, the collar 420 can relax toward its original size. When the cap 150 is disposed over the head 370 of the post 140 such that the head 370 is within the recess 400 of the cap 150, the cap and post are said to be in a covered configuration. When the head 370 of the post 140 is exposed, i.e., when the head 370 is not within the recess 400 of the cap 150, the cap and post are said to be in an uncovered configuration. Because removing the head 370 of the post 140 from the cap 150 will require forcing the head 370 back through the collar 420 of the cap 150, the cap will tend to remain in a covered configuration upon the post 140 unless purposefully removed.

Figure 6E:
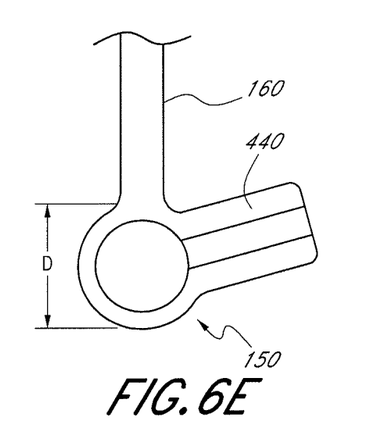
FIG. 6E is a detail of the cap of the base of FIG. 5.
Figure 6F:
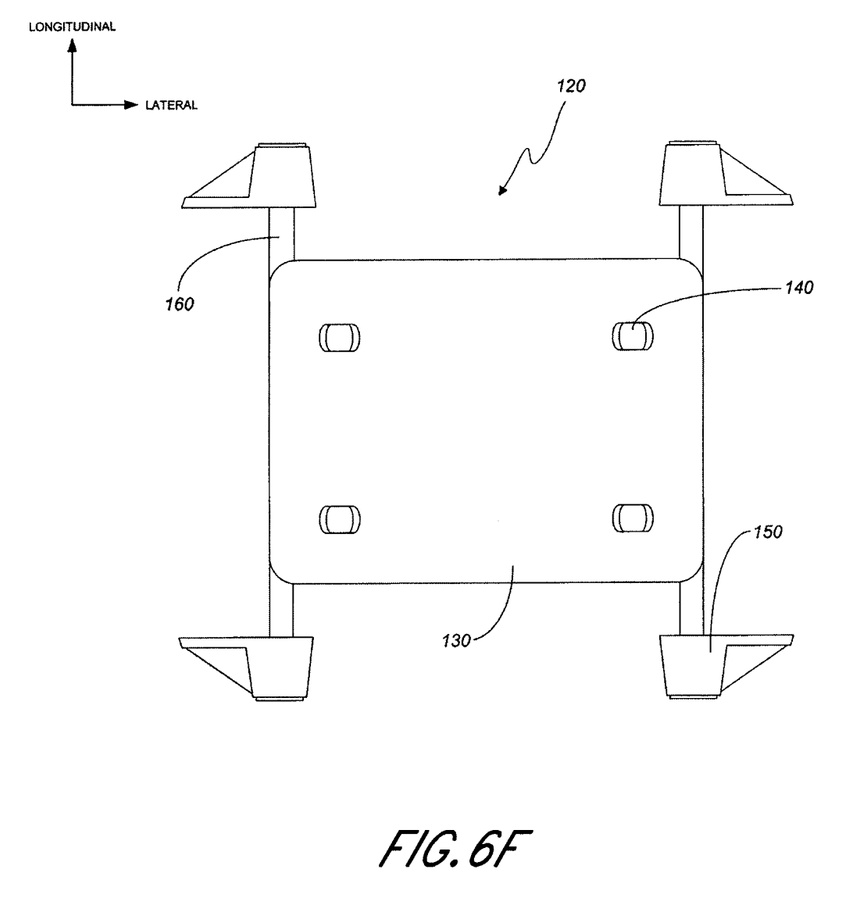
FIG. 6F is a top view of another embodiment of a securement device in accordance with this disclosure.

It should also be noted that the outer dimension of the cap 150, identified as dimension "D" in FIG. 6E, is preferably larger than the size of the openings of the medical article or fitting to be secured. This allows the cap 150, once snapped over the posts 140 into the covered configuration, to inhibit any motion of the medical article in the transverse direction that would allow the post to be removed from the opening of the medical article. The cap 150 can also include a finger tab 440 or other extension to simplify removal of the cap 150 from the posts 140 by a medical practitioner to re-establish the uncovered configuration. As can be seen most clearly in FIGS. 6 and 6E, the tab 440 can extend from the lower portion of the cap 150 away from the center of the cap. The tab 440 preferably extends far enough that a medical practitioner can easily press upward upon the tab 440 in order to snap the cap 150 off of the head 370 of the post 140.

The cap 150 can preferably be made from a material which is at least slightly flexible in order to accommodate the necessary bending, stretching or other deformation which will be required to pass the head 370 or other protrusion through the collar 420. However, the material should also be sufficiently elastic to return towards its original configuration once the head 370 of the post 140 is within the recess 400. In an alternate application, the cap 150 can be made from a substantially rigid material, and the post 140, or at least the head 370 of the post, can be constructed from a material which is appropriately flexible and elastic.

As illustrated in the figures, each cap 150 can be attached to the base 130 in order to prevent the inadvertent loss of the caps 150. This can be accomplished by the use of a flexible coupling, such as a leash 160, shown most clearly in FIGS. 6 and 6A. The leash 160 can take any number of forms to mechanically connect the cap 150 to the base 130 of the retainer 120 while permitting movement of the cap 150 relative to the post 140 for engagement and disengagement of the cap upon the post.

In the illustrated embodiment, the leash 160 comprises a band of flexible material. The leash preferably is integrally molded with the base 130 and the cap 150. The illustrated leash has a width of about 0.5 mm to 5 mm, preferably about 1.5 mm, and a thickness of about 0.5 to 1 mm. The length of the leash depends in part upon the height of the post 140. Preferably, the leash 160 is longer than the height of the post 140, to allow some leeway in engaging or disengaging the cap 150 with the post, as will be understood by one of skill in the art in view of the disclosure herein. While the leash preferably is generally oblong or rectangular in cross-section, as illustrated, it will be understood that the leash can also have other shapes, e.g., a string-like or rounded configuration. It is also possible that a leash 160 made from a separate material which is then attached to the cap 150 and base 130 can be used.

Operation

In use, a medical practitioner can secure a medical article, such as a catheter, or the fitting of a medical article, to a patient using the above-described securement device 100, or a readily apparent modification thereof. The medical attendant first removes the caps 150 from the heads 370 of the posts 140 (if not already done) so as to expose the shaft 350 of each post in the uncovered configuration. Once the posts 140 are uncovered, a catheter or other medical article can be transversely aligned over the base 130. If the medical article includes holes or other openings, these can be slid, pressed or snapped onto the posts 140, as appropriate. If the size of the holes in the medical article is such that they are smaller than the diameter of the head 370 or other protrusion of the post 140, this will create an arrangement whereby the medical article, once snapped over the head 370 of the post 140, will remain upon the post 140 until removed.

Once the medical article or fitting is in position upon the posts 140 of the device 100, the caps 150 can be placed over the heads 370 of the posts 140 and snapped into the covered configuration. The caps 150 are held in position on the posts 140 by the head 370 pressing past the collar 420 of the cap 150. By snapping the caps 150 over the posts 140, the fitting or medical article is inhibited from slipping off of the top of the posts 140. In this way, the medical article is secured upon the device in the transverse direction. Although the medical article is now secured in the transverse, lateral, and longitudinal directions upon the securement device 100, there may be some range of motion available in each of these directions, particularly if the holes of the medical article are larger than the size of the shaft 350 of the posts 140. It will be understood by those of skill in the art that this small amount of free play will not compromise the releasable securement function of the device.

The device can then be positioned over the skin of the patient, and the pull tab of the liner used to remove the liner from a portion of the anchor pad. With the lower adhesive surface of the anchor pad exposed, it can be placed upon the skin of the patient at the appropriate location. The remainder of the liner can then be removed and the anchor pad fully placed upon the patient.

It should be noted that in many applications, it can be preferable to place the anchor pad upon the skin of the patient before attaching the medical article to the base of the device. This may depend upon whether the medical article is already fixed in relation to the patient (e.g., if an IV line is already inserted into the vein of a patient), or whether the medical article is still free to be repositioned.

If the need arises to remove the medical article from the patient, the caps 150 can be snapped off of the heads 370 of the posts 140 to establish the uncovered configuration, and the medical article or fitting removed from the posts 140. This can be preferable in order to change the retaining device, reposition the medical article, change the medical article, or simply to clean the area where the device is secured. The releasable nature of the caps over the posts makes it possible to secure and release the medical article or fitting from the device repeatedly, without the need for sutures or tape.

The securement devices, techniques for use, and variations in each that are described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the devices or techniques described herein. Thus, for example, those skilled in the art will recognize that the devices may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. For example, variations in the design of the head of the posts that result in a more flexible head (e.g., the use of a slot on the post) may be combined with systems in which the caps are attached to the base of the retainer by a separate, rather than integral, leash. These various aspects of the device design, as well as other known equivalents for any of the described features, can be mixed and matched by one of ordinary skill in this art to produce securement devices and techniques in accordance with principles of the system described herein.

Although these techniques and systems have been disclosed in the context of certain embodiments and examples, it will be understood by those skilled in the art that these techniques and systems may be extended beyond the specifically disclosed embodiments to other alternative embodiments and/or uses and obvious modifications and equivalents thereof. Thus, it is intended that the scope of the systems disclosed herein disclosed should not be limited by the particular disclosed embodiments described above, but should be determined only by the scope of the claims that follow.

What is claimed is:

1. A retainer for securing a medical article to the skin of a patient, the retainer comprising:
   a base having a lower surface and an upper surface;
   two posts disposed on the base, each post having a shaft and a protrusion disposed near a distal end of the shaft;
   a receiving area disposed on the base and between the two posts; and
   two caps, each cap being attached to the base by a flexible connection and having an internal recess, each cap being movable between a covered configuration in which the protrusion is engaged with the recess of the cap, and an uncovered configuration, wherein the protrusion is held within the recess of the cap by a snap-fit arrangement between the protrusion and the cap.

2. The retainer of claim 1, wherein each cap further comprises an opening disposed at an open end of the recess, the opening being narrower than the recess.

3. The retainer of claim 1 further comprising an anchor pad supporting the retainer and having an upper surface and a lower surface, at least a portion of the lower surface being covered by an adhesive.

4. The retainer of claim 1, wherein each cap comprises a tab that extends from the cap to provide a surface upon which a medical practitioner may press to remove the cap from the post when the cap is in the covered configuration.

5. The retainer of claim 1, wherein the base has a rounded shape.

6. The retainer of claim 1, wherein the protrusion of each post extends to the same extent around the entire circumference of the post.

7. The retainer of claim 1, wherein the protrusion of each post extends in a lateral direction from the post.

8. A method of releasably securing a medical article to a patient, the method comprising:
   providing a medical article having an elongated body;
   providing a retainer having a base, two posts, and two caps, the two posts being disposed on the base and defining a receiving area there between, each post having a shaft and a protrusion disposed near a distal end of the shaft, each cap being attached to the base by a flexible connection and having an internal recess, each cap being movable between a covered configuration in which the protrusion is engaged with the recess of the cap, and an uncovered configuration;
   placing the medical article on the receiving area such that the medical article is disposed at least partially between the two posts; and
   moving the two caps to the covered configuration, wherein the protrusion is held within the recess of the cap by a snap-fit arrangement between the protrusion and the cap.

9. The method of claim 8, wherein the medical article comprises at least one hole disposed to a lateral side of the elongated body.

10. The method of claim 9 further comprising inserting at least one post through the at least one hole of the medical article.

11. A securement system comprising:
    medical article including a pair of apertures; and
    a retainer comprising:
       base,
       a first post and a second post disposed on the base and configured to extend through the pair of apertures, each of the first and second posts having a shaft and a protrusion disposed near a distal end of the shaft,
       a receiving area disposed on the base and between the first post and the second post to receive at least a portion of the medical article,
       at least one cap being movable in a direction parallel to the shaft when moving from an open configuration to a closed configuration and having a recess and a collar, the recess engaging the protrusion of at least one of the first and second posts after the protrusion passes through the collar when the cap is moved to the closed configuration so as to inhibit movement of the cap back to the open configuration, wherein the protrusion is held within the recess of the cap in the closed configuration by a snap-fit arrangement between the protrusion and the cap.

12. The securement system of claim 11, wherein the at least one cap is attached to the base by a flexible connection.

13. The securement system of claim 11, wherein the collar is disposed at an open end of the recess and is narrower than the recess.

14. The securement system of claim 11 further comprising an anchor pad supporting the retainer, the anchor pad having a surface at least partially covered by adhesive.

15. The securement system of claim 11, wherein the at least one cap comprises a tab against which a medical practitioner may press to remove the at least one cap from the first post.

16. The securement system of claim 11, wherein the protrusion extends to the same extent around the entire circumference of the first post.

17. The securement system of claim 11, wherein the protrusion extends in a lateral direction from the first post.

18. The securement system of claim 11, wherein at least a portion of the shaft of the first post has a diameter.

* * * * *